United States Patent [19]

Chu et al.

[11] Patent Number: 5,040,410
[45] Date of Patent: Aug. 20, 1991

[54] RHEOMETER

[75] Inventors: Benjamin Chu, Setauket, N.Y.; Rolf Hilfiker, Basel, Switzerland

[73] Assignee: The Research Foundation of State University of New York, Albany, N.Y.

[21] Appl. No.: 435,705

[22] Filed: Nov. 13, 1989

[51] Int. Cl.$^5$ ............................................. G01N 11/02
[52] U.S. Cl. .......................................... 73/54; 73/57; 73/59
[58] Field of Search ............................... 73/54, 57, 59

[56] References Cited

U.S. PATENT DOCUMENTS

| 3,635,678 | 1/1972 | Seitz et al. | 23/230 R |
| 3,967,934 | 7/1976 | Seitz et al. | 23/253 R |

OTHER PUBLICATIONS

M. Adam et al., Rev. Phys. Appl. 19, 253 (1984).
B. Gauthier-Manuel et al., J. Phys. E 17, 1177 (1984).
N. A. Park et al., Warm-un Stoffubertragung 18, 201-206 (1984).

Primary Examiner—Hezron E. Williams
Assistant Examiner—William Francos
Attorney, Agent, or Firm—Hoffmann & Baron

[57] ABSTRACT

A magnetic sphere or needle rheometer which may be fully controlled by a personal computer is provided. The rheometer is capable of measuring viscosities in the range of $5 \times 10^{-4}$ to $5 \times 10^4$ Pas (0.5 cP to $5 \times 10^7$ cP). It can operate at shear rates between $1$ s$^{-1}$ and $2 \times 10^{-4}$ s$^{-1}$ and measure relaxation times down to 100 ms. The rheometer includes a magnetic coil which is used to maintain the sphere or needle in a selected position within a sample cell. The current required to maintain the sphere or needle in this position as the sample cell is moved up or down is measured. The viscosity of the liquid can be calculated from the difference in current flowing through the coil when the cell is stationary and when it is moved at a constant velocity.

23 Claims, 6 Drawing Sheets

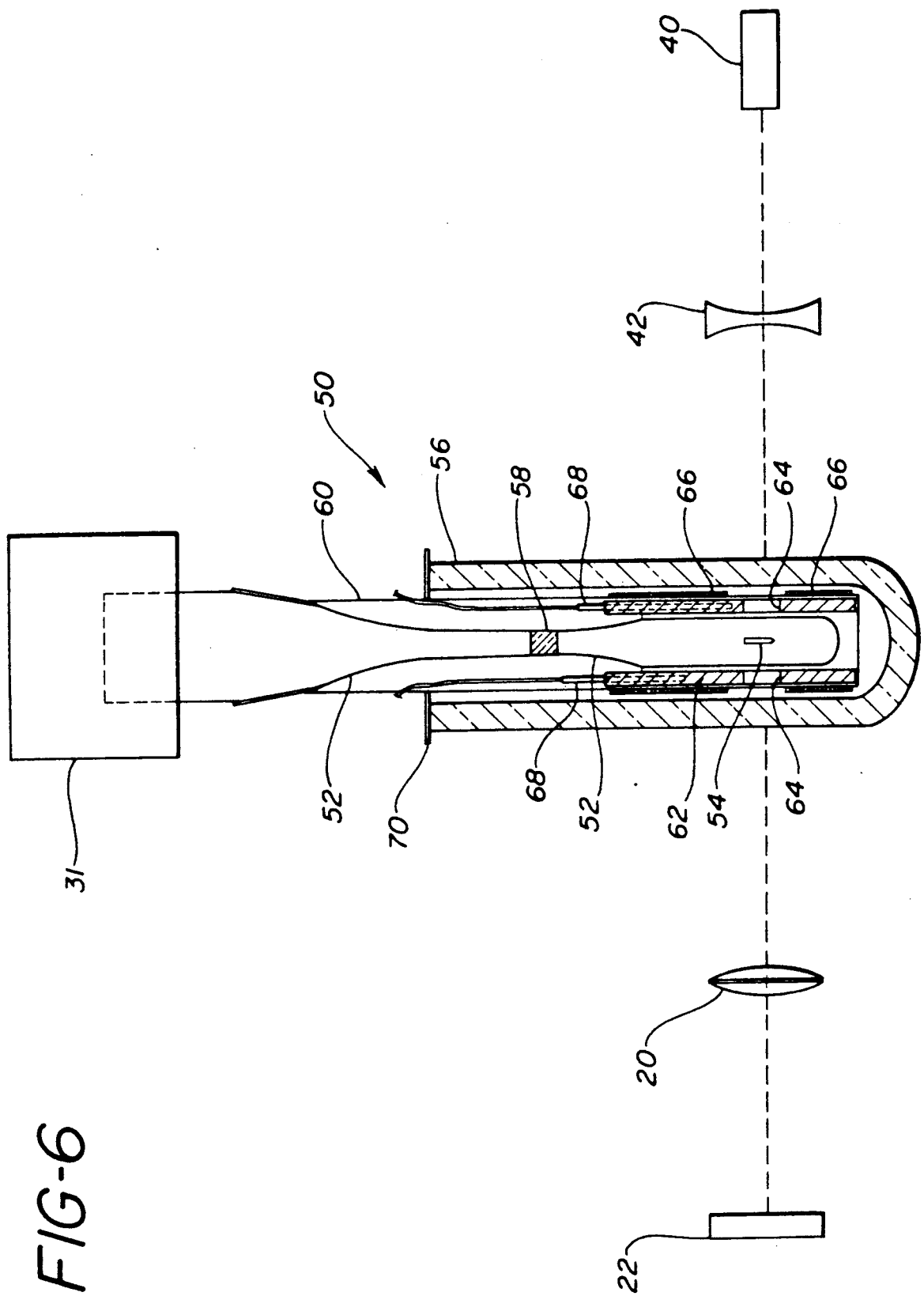

RHEOMETER

This invention was made with government support under Contract Number DAAL038TK0136 awarded by the U.S. Army Research Office. The government has certain rights in the invention.

BACKGROUND OF THE INVENTION

1. Field of the Invention

The field of the invention relates to rheometers of the type where a magnet is maintained at a constant level by the action of a magnetic field.

2. Brief Description of the Prior Art

Viscous and viscoelastic properties of liquids, gels and polymer melts can be determined by a variety of types of rheometers. For liquids with low viscosities the most commonly used apparatus is the Ubbelohde viscometer. Coneplate viscometers conveniently give information about the shear rate dependence of viscosities of liquids. In general, rheological devices that measure viscoelastic moduli impose a periodic shear rate on the material and measure the corresponding shear stress, from which the elastic moduli can be calculated. Certain prior art rheometers operate by maintaining a magnetic sphere in levitation within a tube through the use of a magnetic coil. The tube is displaced at a constant velocity while the force required to maintain the sphere in position is measured. The advantages of such devices are that the shear rate can be varied over a very wide range and to very low values (e.g. $2 \times 10^{-4}$ s$^{-1}$), and that they can be used to measure elastic properties of fluids, melts and gels.

SUMMARY OF THE INVENTION

It is an object of the invention to provide a rheometer capable of measuring viscosities with greater precision than existing equipment.

It is another object of the invention to provide a relatively inexpensive rheometer which is easy to use and provides accurate results.

In accordance with these and other objects of the invention, a rheometer is provided which operates by suspending a magnetic sphere or needle assembly in a sample with the help of a magnetic field gradient produced by a coil or the like through which a current is flowing. The electric current is proportional to the force which is necessary to keep the sphere or needle at a fixed position in the sample cell. Means are provided for moving the sample cell up or down while the sphere or needle is maintained in position. The force acting on the magnet is comprised of the gravitational force, buoyancy and viscoelastic force. It is therefore possible to calculate the viscosity and viscoelastic properties of the sample from the difference in current which is necessary to keep the sphere or needle at its null position when the sample cell is still and when it is moving at a constant known speed.

In accordance with a preferred embodiment of the invention, the magnet is illuminated by a laser beam. The position of the magnet is detected by a quadrant detector. A magnified image of the magnet is produced on the detector through the use of a lens.

The components of the rheometer are preferably controlled by a personal computer. A plurality of current readings may be taken during each run as the sample cell is moved. These readings may then be averaged.

A sample cell is also provided by the invention which allows measurements to be taken at high temperatures. The cell is positioned within an insulator such as a Dewar vessel. Heating coils are wound around the cell, preferably one coil above and one below the position of the suspended magnet. A metal cylinder is preferably positioned inside a quartz tube, the sample cell within the metal cylinder, and the heating coils wound around the quartz tube. Windows within the cylinder allow observation of the suspended magnet.

BRIEF DESCRIPTION OF THE DRAWINGS

FIG. 6 is a schematic diagram of a high temperature chamber for use as part of a rheometer.

DETAILED DESCRIPTION OF THE INVENTION

Figure 1:
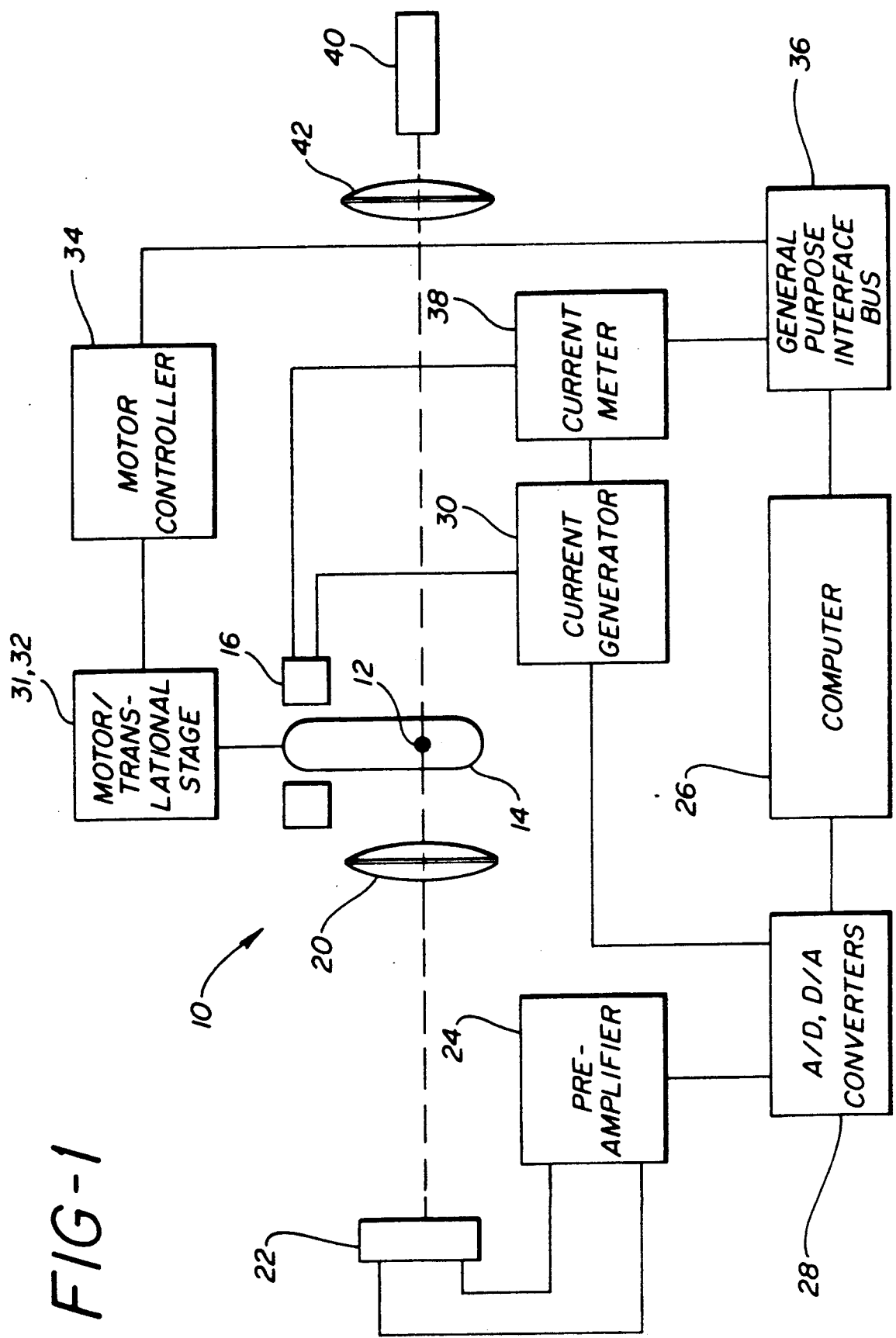
FIG. 1 is a schematic illustration of a rheometer in accordance with the invention.

FIG. 1 shows a schematic representation of a magnetic sphere rheometer 10. A Sm-Co (Samarium-Cobalt) magnetic sphere 12 having a diameter of about one millimeter is suspended in the fluid of interest in the sample cell 14. The force which is necessary to keep the sphere levitated is furnished by a magnetic coil 16.

Figure 2:
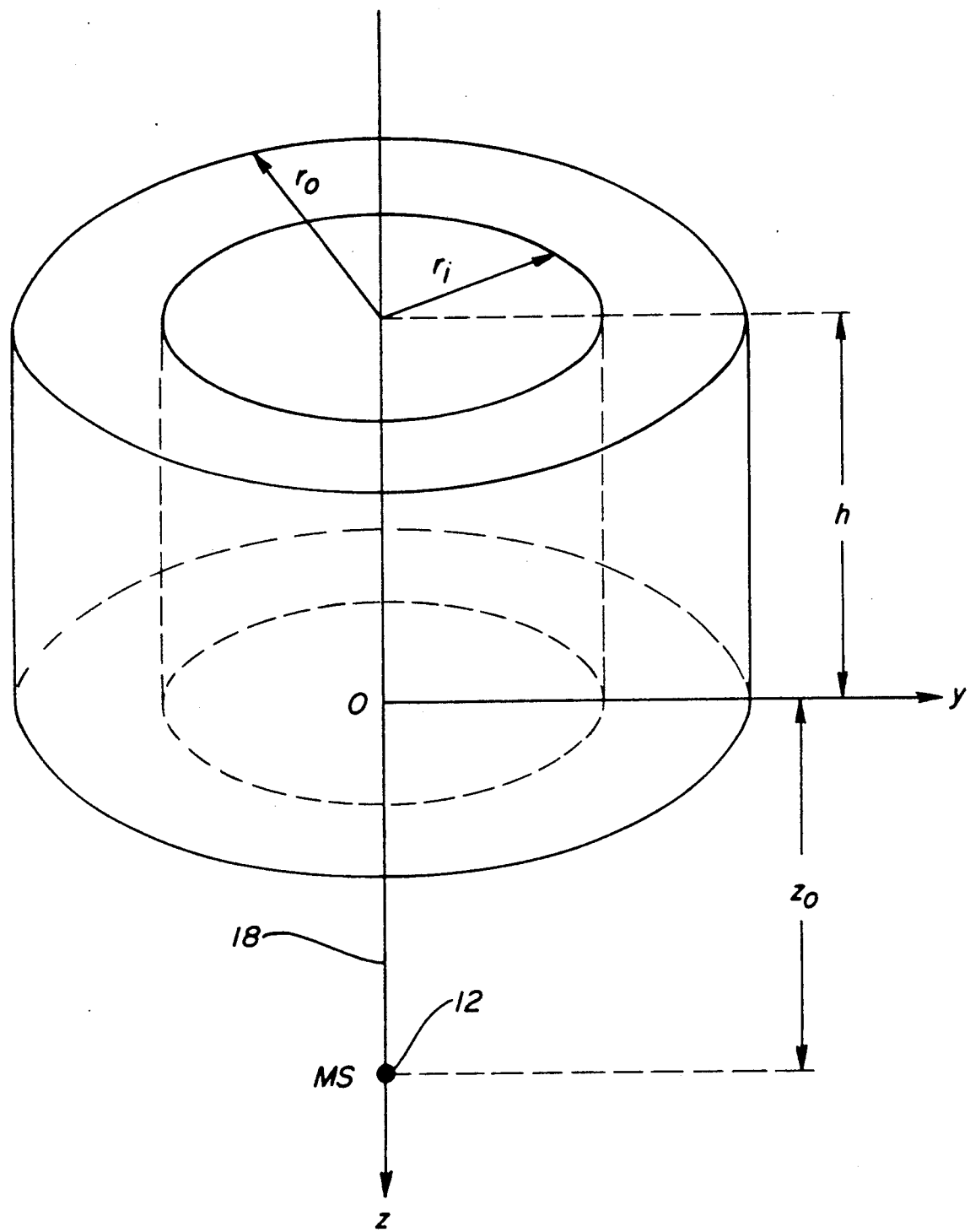
FIG. 2 is a schematic illustration of a magnetic coil with respect to a magnetic sphere.

An electric current (I) flowing through a circular loop with a radius r produces a magnetic field (H) on the axis of symmetry 18 of the loop, as shown in FIG. 2. At a distance z from the intersection of the axis of symmetry with the plane containing the loop, the magnitude of $H_z$ at position z is given by:

$$H_z(z) = 0.5 r^2 I / (r^2 + z^2)^{1.5}. \tag{1}$$

From Eq. (1), the mag short thick coil can be calculated if it is assumed that the coil consists of a series of independent current loops. For a coil with an inner radius $r_i$, an outer radius $r_o$ and a height h, as shown in FIG. 2, the magnetic field gradient (dH/dz) along the z-axis at a distance $z_o$ from the lower rim of the coil is then:

$$\left( \frac{dH}{dz} \right)_{z=z_o} = -1.5 \, I n_o \int_{r=r_i}^{r_o} \int_{z=z_o}^{z_o+h} \frac{zr^2}{(z^2+r^2)^{2.5}} \, dz \, dr, \tag{2}$$

where I is the current flowing through the coil, $n_o$ is the number of windings per unit area in the yz-plane and we have dropped the subscript z for the magnetic field in z-direction. The upward force ($F_{up}$) on the magnetic sphere with a permanent magnet dipole (J) produced by the field gradient is:

$$F_{up} = \frac{4\pi}{3} a^3 J \frac{dH}{dz} = AI. \tag{3}$$

where A is the proportionality constant between $F_{up}$ and I and is governed by Eqs. (2) and (3). The net downward force ($F_{down}$) consists of the following contributions:

$$F_{down} = F_g - F_b + F_e + F_i. \quad (4)$$

In Eq. (4), $F_g$ (=mg) is the gravitational force; $-F_b$ (= $-mg\, p_1/p_5$) is the buoyancy force with $p_1$ and $p_5$ being the densities of the liquid and the magnetic sphere, respectively; $F_e$ is the viscoelastic force originating from the movement of the sample cell in the laboratory fixed coordinate system; and $F_i$ is the viscoelastic force originating from the movement of the magnetic sphere in the same coordinate system. The upward force, $F_{up}$, is used to compensate the downward force, $F_{down}$, in order to keep the sphere at a constant position in the laboratory fixed coordinate system.

With the help of lens 20, an imaging lens with a focal length of 105 mm, a magnified image of the sphere 12 is obtained on the position sensitive detector 22. The position sensitive detector yields an output signal which is proportional to the deviation of the sphere from a null position. This signal is amplified by a preamplifier 24 and read by a computer 26 via an A/D interface 28. The computer acts as a proportional, differential and integral regulator and produces an analog output voltage (U(t)) via a D/A interface. The sum of a constant voltage $U_o$ and U(t) is used to control the current output of a current generator 30. The magnetic force is proportional to the current flowing through the coil 16. Thus, the described setup can be used to levitate the magnetic sphere 12 under a variety of conditions. When the magnetic sphere is kept at a constant position in the laboratory fixed coordinate system, e.g., when the sphere is stationary at its null position, $F_i = 0$ for a viscous fluid. When the viscous fluid is stationary (with the magnetic sphere in its null position), $F_e = 0$. Then, $F_{down} = F_{g-Fb}$.

The sample cell 14 is mounted on a translational stage 31 which is driven by a stepping motor 32. The sphere 12 is maintained at a fixed point in space. The shear stress is produced by moving the sample cell 14 along the z-axis with a velocity (v). The motor 32 is controlled by a motor controller 34 which in turn receives commands from the computer 26 via a general purpose interface bus (GPIB) 36. The current (I) flowing through the coil is proportional to $F_g - F_b + F_e$ and is measured by the current meter 38 which is read by the computer via a GPIB interface 36.

The measured current difference between the state when the cell 14 is moved at a constant speed and the equilibrium position, i.e., when the cell is stationary, is proportional to the viscoelastic force.

$$F_e = A[I(v, \Delta z) - I(v=0, \Delta z=0)], \quad (5)$$

where $\Delta z$ is the displacement of the cell in the z-direction (cf. FIG. 2) and v=dz/dt. I(v, $\Delta z$) denotes the current required to levitate the sphere 12 when the liquid is moving at a velocity v over a distance $\Delta z$. For viscous liquids, I(v, $\Delta z$) is a function of v and not $\Delta z$. I(v=0, $\Delta z$=0) denotes the equilibrium value.

For a sphere of radius (a) moving in a liquid with a velocity v, shear rate and shear stress cannot be calculated explicitly. However, the maximum shear rate at the surface of the sphere can be estimated as $\gamma = 3v/2a$. The viscosity ($\eta$) of a Newtonian liquid is related to the shear force ($F_s$) by the well known Stokes law:

$$F_s = 6\pi a \eta v. \quad (6)$$

$F_e = F_s$ for viscous liquids. By combining Eqs. (5) and (6), it follows that $$\eta = \frac{A}{6\pi a} \frac{\Delta I}{v}, \quad (7)$$

where $\Delta I = I(v, \Delta z) - I(v=0, \Delta z=0)$ and $(A/(6\pi a))$ becomes the experimentally determined proportionality constant by using liquids of known viscosity.

For a Newtonian liquid, the Stokes law applies for laminar flow, i.e.

$$F_e(t) = \Phi a \eta v(t). \quad (8)$$

Figure 3A:
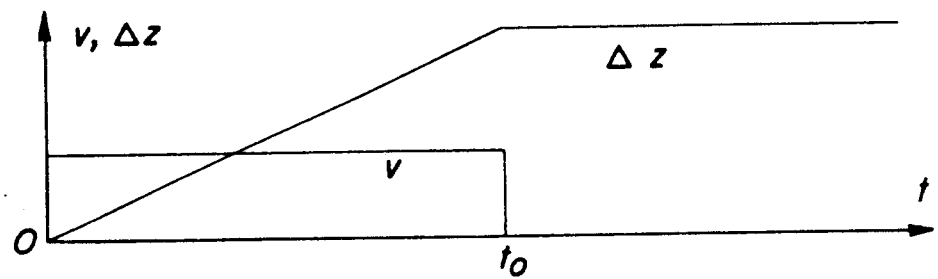
FIGS. 3a–e represent the movement of a magnetic sphere as a function of time, and the current response in viscous liquids, elastic solids, viscoelastic liquids, and viscoelastic solids, respectively.
Figure 3B:
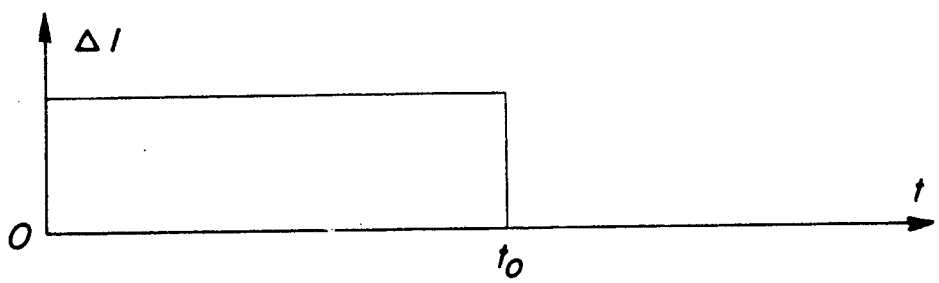

$\Phi$ is equal to $6\pi$ if the radius of the sphere (a) is much smaller than the dimensions of the sample cell and the sphere is far away from both the bottom of the cell and the surface of the liquid. If these requirements are not met, the value of $\Phi$ is different from $6\pi$. The correction terms can be calculated. In the case of a Newtonian liquid, the current response to a discontinuously varying shear rate (FIG. 3a) has the form shown in FIG. 3b.

Figure 3C:
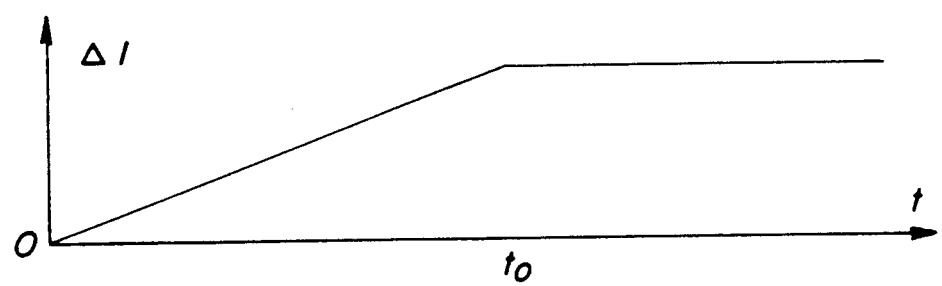

In a purely elastic solid, the force which is necessary to keep the sphere at its null position after moving the sample cell over a distance ($\Delta z$) is proportional to the displacement, i.e.

$$F_e(t) = \Phi a G_\infty \int_0^t v(t')dt' = \Phi a G_\infty \int_{z_0}^{z_0 + \Delta z} dz = \Phi a G_\infty \Delta z(t), \quad (9)$$

where $\eta v$ is replaced by $G_\infty \int v(t)dt$, with $G_\infty$ being the static elastic modulus which is independent of time (cf. FIG. 3c).

In general, the elastic modulus of a viscoelastic fluid or solid is frequency or time dependent. The dynamic viscosity, $\eta(t)$, is related to the elastic modulus by:

$$\eta(t) = \int_0^t G(t')dt'. \quad (10)$$

The force which is necessary to keep the sphere at a constant position after applying a constant shear rate in a viscoelastic liquid can thus be described by:

$$F_e(t) = \Phi a v \int_0^t G(t')dt'. \quad (11)$$

Figure 3D:
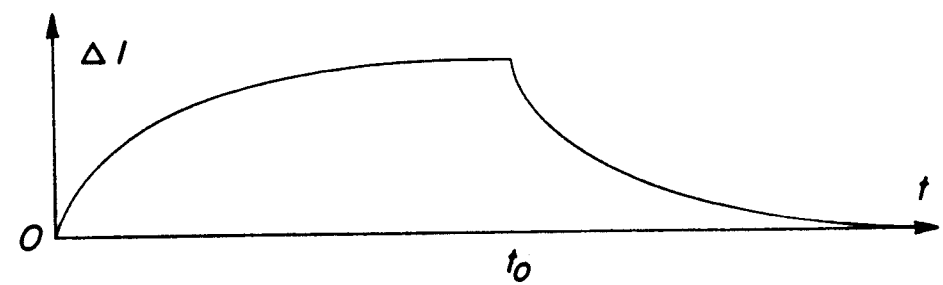

For times much longer than the longest relaxation time ($\tau$), Eq. (11) becomes identical to Eq. (8). FIG. 3d elucidates the situation graphically. If the shear rate is reduced to zero after a time $t_o$, the force relaxes to zero according to the following equation:

$$F_e(t) = \Phi a v \left( \int_0^{t_o > \tau} G(t')dt' - \int_{t_o}^t G(t' - t_o)dt' \right). \quad (12)$$

Figure 3E:
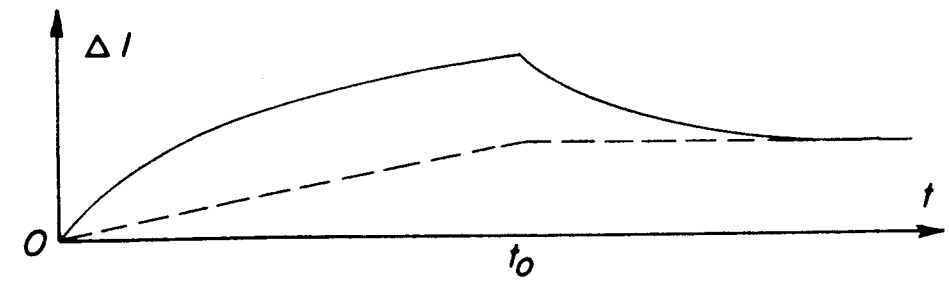

For viscoelastic solids, the total force is the sum of the viscoelastic force (cf. Eqs. (11) and (12)) and the elastic force (cf. Eq. (9)) with v having a constant speed. The ΔI curve is displayed in FIG. 3e, in which the elastic force contribution is denoted by the dashed line. The total force for $t < t_o$ is:

$$F_e(t) = \Phi a v \int_0^t G(t')dt' + \Phi a G_\infty \int_0^t v(t')dt'. \quad (13)$$

For times larger than $t_o$, Eq. (13) has to be replaced by Eq. (14) (cf. FIG. 3e).

$$F_e(t) = \Phi a \left[ G_\infty \int_0^t v(t')dt' + v \left( \int_0^{t_o > \tau} G(t')dt' - \int_{t_o}^t G(t' - t_o)dt' \right) \right]. \quad (14)$$

If the behavior of the viscoelastic liquid can be described by the Maxwell model with a single relaxation time $\tau_r$, i.e., $$G(t) = G_o e^{-1/\tau F}, \quad (15)$$

we get from Eqs. (10) and (15):

$$\eta(t) = \int_0^t G(t')dt' = \eta_\infty [1 - \exp(-t/\tau_r)], \quad (16)$$

where $\eta_\infty = G_o \tau_r$. The relaxation time $\tau_r$ can thus be obtained from measurements of the time dependence of $F_e$ and the static viscosity ($\eta_\infty$) from the steady state value of the current.

The computer 26 has a threefold function: (a) it gives commands to the motor controller 34, setting the distance of displacement Δz and the speed of displacement v. At the same time it checks if the actual speed is equal to the set speed; (b) it reads the current from the current meter 38 and writes the values it has read together with the corresponding time of the reading into a data file; (c) it reads the position error and uses this signal to control the output current of the current generator 30. For the control cycle, the following algorithm is used:

$$U_n = U_{n-1} + K_i U_{err}(n), \quad (17)$$

$$U(n) = U_n + K_a U_{err}(n) + K_d[U_{err}(n) - U_{err}(n-1)], \quad (18)$$

where $U_{err}$ is the digitized error signal, $U(n)$ is the output voltage which controls the current and $K_a$, $K_d$ and $K_i$ are the coefficients for the proportional, differential and integral correction, respectively. $U_{err}$ is the digitized output voltage of the preamplifier 24 and is proportional to the deviation of the magnetic sphere 12 from its null position. $K_a U_{err}$ is a component of the voltage output from the computer to the current generator 30. It is proportional to the deviation of the magnetic sphere 12 from its null position and is used to move it in the direction of the null position. The difference of error signals in two consecutive readings, $U_{err}(n) - U_{err}(n-1)$, is proportional to the speed of the magnetic sphere. Thus, $K_d(U_{err}(n) - U_{err}(n-1))$, is a component of the voltage output from the computer to the current generator 30 for the purpose of slowing down the movement of the magnetic sphere. Eq. (17) forces the magnetic sphere to the preassigned null position so that the time-average of $U_{err}$ is zero. Depending on the viscosity of the system, $K_a$, $K_d$ and $K_i$ must be adjusted to their respective optimal values, so that the sphere is kept at a stable position. These adjustments can be made while the program is running. The computer performs approximately 400 correction cycles per second.

The A/D, D/A interface 28 operates with a precision of 12 bit. U(t) is therefore controlled within an accuracy of ≈0.03%. In principle, the bias voltage $U_o$ can be set to a value such that it produces a current which counterbalances $F_g$ and $F_b$. In that case U(t) controls the additional current which is necessary to establish $F_e$. In other words, $F_e$ can, in principle, be controlled to an accuracy of ≈0.03%.

Figure 4:
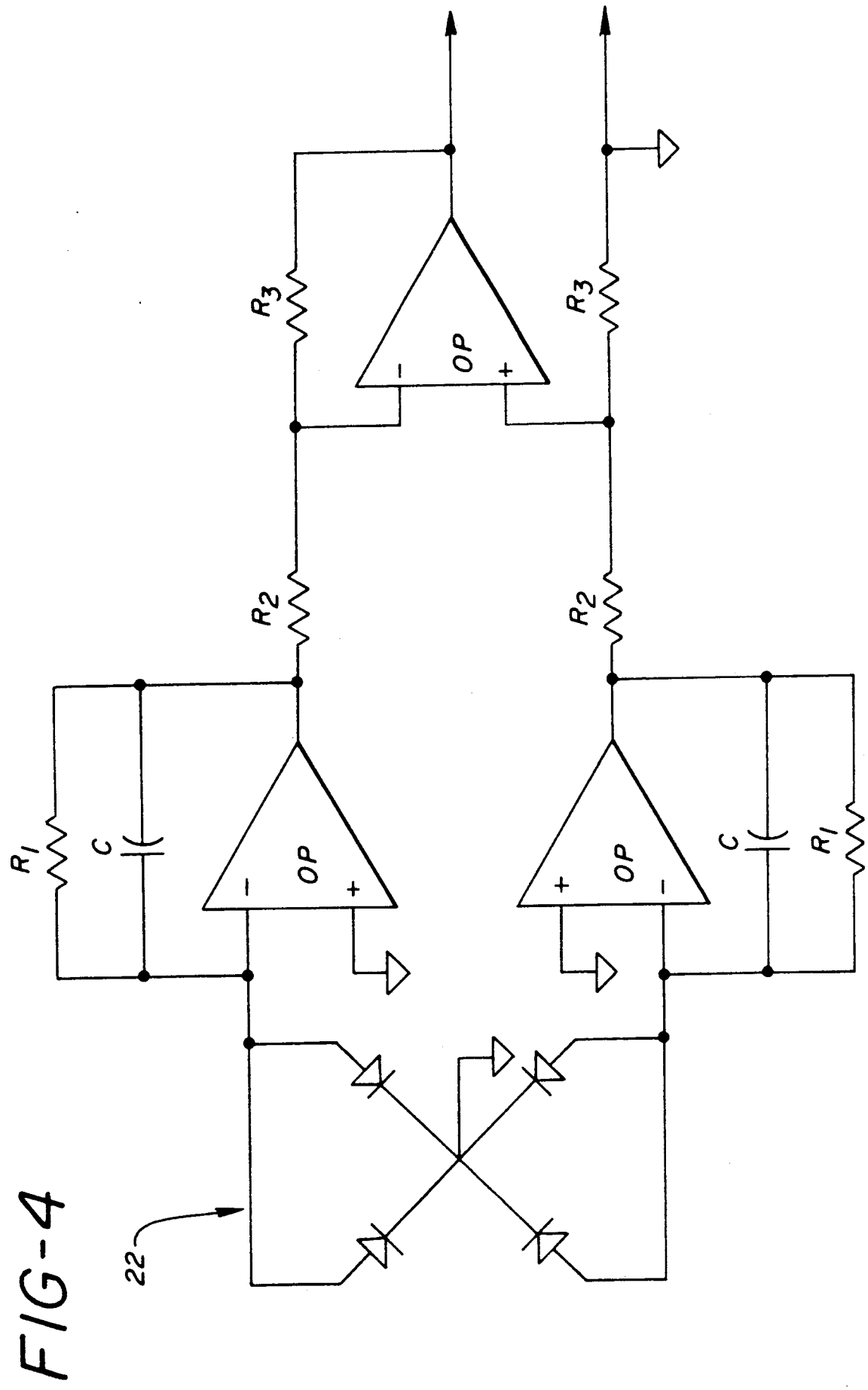
FIG. 4 is a schematic circuit diagram of a photodiode preamplifier.

The output of the position sensitive detector 22 is amplified by the preamplifier as shown in FIG. 4, so that a position change of 1 μm of the magnetic sphere produces a change of ≈100 mV in the output signal of the preamplifier. The output signal is read with a precision of 12 bit/10 V, allowing a precision of 3 nm in the determination of the position of the sphere by means of a quadrant detector. As shown in FIG. 4, the two upper quarters and the two lower quarters of the detector are, respectively, connected in series, so that it acts as a lateral position sensor. The amplified difference of the output current of the top half and the bottom half is proportional to the deviation of the sphere from its null position. This difference is read by the computer, which regulates the current flowing through the coil. The values of $R_1$, $R_2$ and $R_3$ are, respectively, 909KΩ, 10KΩ and 82.5KΩ. The capacitor C has a capacitance of 100 pF.

The translational stage used in this illustrative embodiment has a step length of 0.1 m and is controlled by the motor controller 34 which allows steprates up to 4000 steps per second. The motor is driven in ministeps (1/10 step). Therefore it is possible to go to speeds as low as one step per second (0.1 μms$^{-1}$) and still have a quasticontinuous motion.

The current meter 38 is commercially available and reads the current with an accuracy of 5 ppm. The current is generated by a bipolar power supply/amplifier. A 3 mW He-Ne laser 40 is used to illuminate the magnetic sphere. The sphere, which is black, accordingly will absorb less power than if a standard lamp is employed. A lens 42 is necessary to expand the beam diameter so that it is about fifteen times as large as the magnetic sphere. This lens 42, which has a focal length of 50 mm, expands the beam diameter to about 1.5 cm at the magnetic sphere. The sample cell 14 is cylindrical with an inner diameter of 10 mm and a screwtop with a Teflon washer which seals the cell hermetically. The sample cell may be immersed in silicon oil which is thermostatted by a water jacket (not shown). A circulating bath adjusts the water temperature to ±0.05 K at room temperatures.

The use of a high precision position detector, current meter, current generator, the very sensitive control of the current generator, and the ability to average the current readings over several hundred to thousand readings per run, allow one to measure the viscosity of a liquid with $\eta = 10$ P to a precision of 0.3%. With more viscous samples an even higher precision can be achieved. The use of a quadrant detector is superior to the use of two photodiodes and two prisms which split the image into two halves. It also eliminates a source of reflections and stray light produced by the prisms. Control of the test procedure by a personal computer facilitates automation and makes it very easy to adapt it to different situations. It is also a cost saving factor because it no longer requires the purchase of a proportional/differential/integral controller. The use of a motor which is driven in ministeps allows one to measure both higher viscosities and go to lower shear rates.

EXAMPLE

The viscosities of semidilute solutions of poly(isobutylmethacrylate-t-butylaminoethylmethacrylate-(poly(IBMA-tBAEMA)) random copolymer in dimethylacetamide (DMAA) and tetramethylethylenediamine (TMEDA), which are both good solvents for the polymer, were determined. The copolymer had a molar ratio of IBMA to tBAEMA of 77:23 and an estimated molecular weight of $2.7 \times 10^6$ gmol$^{-1}$.

The solutions were prepared by mixing polymer and solvent and agitating the sample gently for several weeks. By measuring the viscosity at different heights in the sample cell, it was assured that the solution is homogenous on a macroscopic scale. The viscosities of DMAA and TMEDA at 25° C. were determined with an Ubbelohde viscometer. Values of 0.94 and 0.58 cP were found.

In the investigated concentration regime, the measured viscosities could be fitted well with an Arrhenius equation:

$$\eta = r e^{sc} \quad (19)$$

r and s are adjustable parameters. For the solution of the polymer in TMEDA, r and s were 5.8 cP and 61.9 g$^{-1}$cm$^3$, and for DMAA as solvent, r=5.3 cP and s=61.0 g$^{-1}$cm$^3$.

A magnetic "needle" may be employed instead of a sphere. The needle includes a hollow, thin walled precision glass (quartz) capillary having a rod magnet therein. The capillary may have an outside diameter of about one millimeter and an inside diameter of about 0.9 mm. Both ends are sealed, at least one of the ends sealed in such a manner so as to provide a hemispherical tip. If the wall thickness, capillary length and magnet mass are properly chosen, the sensitivity of the magnetic needle can easily be matched to the density of the fluid to within 0.01 gcm$^{-3}$. This allows about a five hundred-fold increase in precision when compared to measurements performed with a solid magnetic sphere at low viscosities.

Figure 5A:
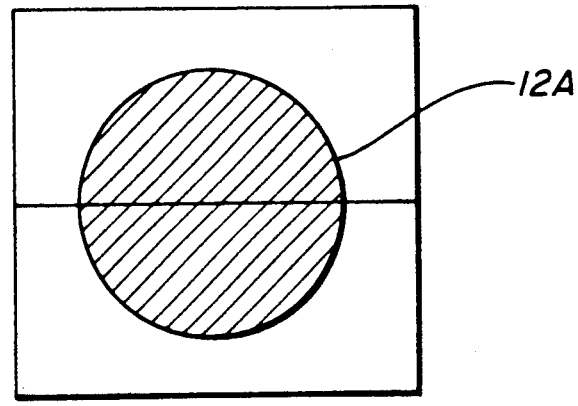
FIGS. 5a–c are illustrations of shaded images of a magnetic sphere, magnetic needle, and a magnetic needle with a part of the top half of a detector obscured by a mask, respectively.
Figure 5B:
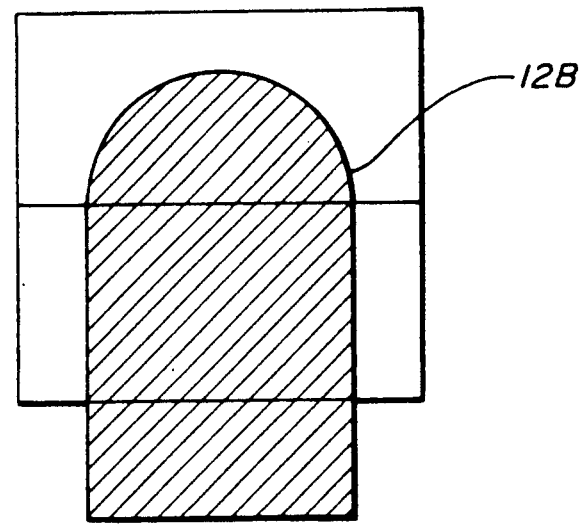
Figure 5C:
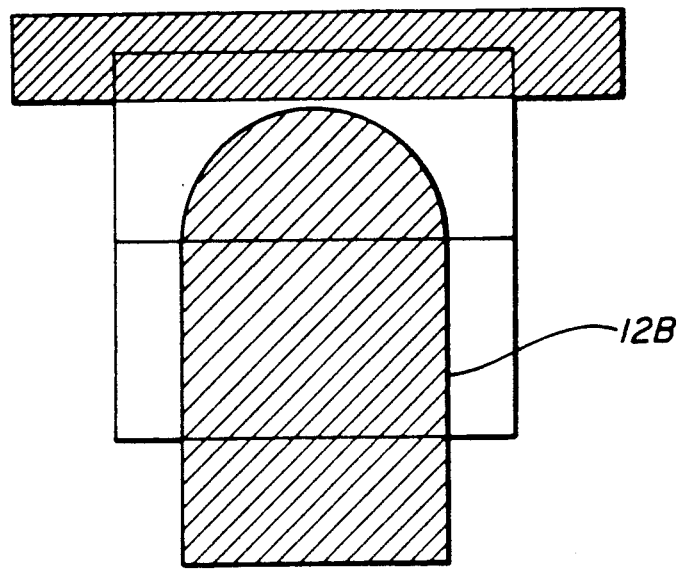

When a sphere is employed, a magnified image 12A thereof, as shown in FIG. 5a, is produced on the quadrant detector by the lens 20. When the sphere is replaced by a needle, the image 12B obtained on the position detector has a form as shown in FIG. 5b. In this situation, the error signal ($U_{err}$) is zero as long as neither the tip nor the tail of the needle are imaged on the detector. Therefore, controlling the current in a way that $U_{err}=0$ would lead to a non-defined position of the needle. This problem can easily be avoided by setting the desired error signal ($U_{err,des}$) in the computer control program to a finite constant value, which is proportional to the difference of the area which is obscured by the needle on the top and the bottom half of the position sensitive detector. Obviously, the position of the needle is then dependent on $U_{err,des}$ and the intensity of the illuminating laser. In the disclosed apparatus, the laser-housing is cooled by thermostatted water, which reduces the long term intensity fluctuations to a negligible value. Alternatively, a part of the top half of the detector can be obscured by a mask (FIG. 5c), so that $U_{err,des}$ can be set to zero again. Problems due to fluctuations in laser intensity can also be avoided by dividing $I_{top}-I_{bot}$ by $I_{top}+I_{bot}$.

Whereas it is not possible to obtain exact solutions for shear rate and shear stress using a sphere moving in a Newtonian liquid with a given velocity, solutions have been obtained for the corresponding case of a needle. If a needle of diameter d moves along the symmetry axis of a cylinder of diameter D which is filled with a fluid of viscosity $\eta$ with a velocity v, the shear rate $\gamma$ and the shear stress ($\sigma$) at the needle wall can be expressed by the equations below if the tip and the tail effects are neglected, $$\gamma = \frac{2v}{d} \frac{b^2 - 1}{b^2 (lnb - 1) + lnb + 1} \quad (20)$$

$$\sigma = \eta\gamma \quad (21)$$

where b=D/d.

A system 50 for measuring viscosities between about $3 \times 10^{-3}$ and $5 \times 10^4$ Pas at temperatures up to 380° C. is shown in FIG. 6. The system includes most of the same components described above, namely a laser source 40, a beam-expanding lens 42, an imaging lens 20, a position sensitive detector 22, and a vertical translational stage 31 capable of moving a sample cell about 0.1 μm per step.

A glass cell 52 is positioned between the lenses 20, 42. A magnetic needle 54 is suspended within the cell 52 by a magnetic field.

The glass cell is preferably positioned within a transparent Dewar flask 56. The Dewar flask provides substantial insulation for the cell 52. A solid glass joint 58 is provided within the neck of the cell to prevent evaporation of solvent from the sample.

A quartz tube 60 is positioned within the Dewar flask 56 and is joined to the sample cell 52. A metal cylinder 62, preferably copper, is positioned within the tube. The cylinder 62 includes a pair of opposing windows 64 aligned with the suspended needle 54. Two separate coils 66 of heating wire are wound onto the quartz tube, one coil above and one below the needle 54. Since the power dissipation of the two coils can be controlled separately, the temperature gradient at the position of the needle (or sphere) can be minimized. It is important that the coils be wound in a non-inductive manner to avoid the production of any magnetic fields by the heater. The metal cylinder 62 within the tube 60 also serves to minimize temperature gradients. Platinum resistors 68 are positioned within the metal cylinder 62 for temperature measurement and control. Thermistors can alternatively be employed for relatively lower temperature applications. Insulation 70 is provided at the top of the Dewar flask 56 for preventing the loss of heat from within the flask. The flask 56 is surrounded by a coil (not shown), which produces the magnetic field gradient.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A rheometer assembly for determining selected physical properties of liquids and gels, comprising:
   a sample cell;
   a magnetic needle which is positionable within said sample cell, said magnetic needle comprising a non-magnetic tube and magnetic material positioned within said tube;
   means for maintaining said magnetic needle at a selected position within said sample cell, said means for maintaining including means for generating a magnetic field;
   a laser source for directing a laser beam towards said sample cell;
   means for expanding a laser beam positioned between said laser source and said sample cell;
   a position detector aligned with said laser source and sample cell, said sample cell being positioned between said laser source and said position detector;
   means for moving said sample cell in a substantially vertical direction; and
   means for determining a physical characteristic proportional to the force necessary to maintain said magnetic needle at a selected position.

2. A rheometer assembly as defined in claim 1 wherein said position detector is a quadrant detector.

3. A rheometer assembly as defined in claim 2 wherein said quadrant detector includes lower left and lower right quadrants connected in parallel.

4. A rheometer assembly as defined in claim 2 including an imaging lens positioned between said sample cell and said quadrant detector.

5. A rheometer assembly as defined in claim 4 wherein said means for moving said sample cell includes a translational stage having a step length of about 0.1 μm.

6. A rheometer assembly as defined in claim 4 including means for obscuring a portion of said quadrant detector.

7. A rheometer assembly as described in claim 1 including means for minimizing the temperature gradient at a selected portion of said sample cell.

8. A rheometer assembly as described in claim 7 wherein said means for minimizing the temperature gradient include first and second separately controllable heating means positioned adjacent to said sample cell and located, respectively, above and below said selected portion of said sample cell.

9. A rheometer assembly as defined in claim 8 including a metal cylinder positioned between said sample cell and said first and second heating means.

10. A rheometer assembly as defined in claim 8 wherein said first and second heating means are heating coils wound in a substantially non-inductive manner.

11. A rheometer assembly as defined in claim 9 including a glass tube, said sample cell and said metal cylinder being positioned within said glass tube, said first and second heating means being positioned outside said glass tube.

12. A rheometer assembly as defined in claim 11 wherein said sample cell, metal cylinder, glass tube and first and second heating means are positioned within a Dewar vessel.

13. A rheometer assembly as defined in claim 1 including a heat conductive cylinder, said sample cell being positioned within said cylinder, and means for heating said cylinder.

14. A rheometer assembly as defined in claim 13 wherein said means for heating said cylinder include a first heat source and a second heat source, said heat sources being spaced a selected vertical distance from each other and adjacent said heat conductive cylinder.

15. A rheometer assembly as defined in claim 14 wherein said heat conductive cylinder includes a pair of opposing windows.

16. A rheometer assembly as defined in claim 14 wherein each of said first and second heat sources is a heating coil.

17. A rheometer assembly as defined in claim 13 including a heat sensor mounted within said heat conductive cylinder.

18. A rheometer assembly as defined in claim 13 including a Dewar vessel, said sample cell and said heat conductive cylinder being positioned within said Dewar vessel.

19. A rheometer assembly as defined in claim 1 including a fluid within said sample cell, wherein the density of said magnetic needle is within about 0.01 gcm$^{-3}$ of said fluid.

20. A rheometer assembly as described in claim 1 wherein said tube of said magnetic needle is a non-metallic tube.

21. A rheometer assembly as described in claim 20 wherein said glass tube has an outside diameter of about one millimeter.

22. A rheometer assembly as described in claim 8 wherein said first and second heating means comprise, respectively, first and second coils of heating wire, said coils being wound in a non-inductive manner to avoid the production of magnetic fields.

23. A rheometer assembly comprising:
   a sample cell;
   means for maintaining a magnetic needle at a selected positioned within said sample cell, said means for maintaining including means for generating a magnetic field;
   a conductive shield positioned about a selected portion of said sample cell, said shield including a pair of opposing windows;
   means for directing a light beam through said pair of opposing windows and said sample cell;
   a position detector aligned with said light source;
   means for controlling the temperature of said selected portion of said sample cell, said means for controlling including first and second separately controllable heating means, said first and second heating means being positioned, respectively, above and below said windows;
   means for moving said sample cell in a substantially vertical direction; and
   means for determining a physical characteristic proportional to the force necessary to maintain the magnetic needle at a selected position between said windows.

* * * * *